United States Patent
Chen et al.

(10) Patent No.: US 11,992,221 B2
(45) Date of Patent: May 28, 2024

(54) OCCLUDER, OCCLUDING SYSTEM AND CONVEYING DEVICE

(71) Applicant: LIFETECH SCIENTIFIC (SHENZHEN) CO., LTD., Guangdong (CN)

(72) Inventors: Xianmiao Chen, Shenzhen (CN); Mingjuan Fu, Shenzhen (CN); Yudu Wang, Shenzhen (CN)

(73) Assignee: LIFETECH SCIENTIFIC (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/776,011

(22) PCT Filed: Jul. 24, 2020

(86) PCT No.: PCT/CN2020/104523
§ 371 (c)(1),
(2) Date: May 11, 2022

(87) PCT Pub. No.: WO2021/120625
PCT Pub. Date: Jun. 24, 2021

(65) Prior Publication Data
US 2022/0395279 A1    Dec. 15, 2022

(30) Foreign Application Priority Data

Dec. 20, 2019 (CN) .......................... 201911329002.4
Dec. 20, 2019 (CN) .......................... 201911330630.4
Dec. 20, 2019 (CN) .......................... 201911330633.8

(51) Int. Cl.
*A61B 17/12* (2006.01)

(52) U.S. Cl.
CPC .. *A61B 17/12172* (2013.01); *A61B 17/12109* (2013.01); *A61B 17/12122* (2013.01); *A61B 2017/12086* (2013.01)

(58) Field of Classification Search
CPC ........ A61B 17/12172; A61B 17/12109; A61B 17/12122; A61B 2017/12086;
(Continued)

(56) References Cited

U.S. PATENT DOCUMENTS 5,192,301 A    3/1993  Kamiya et al.
2004/0153095 A1*  8/2004  Seddon ................ A61B 17/221
606/113

(Continued)

FOREIGN PATENT DOCUMENTS

CN    102805673 A    12/2012
CN    104287803 A    1/2015
(Continued)

OTHER PUBLICATIONS

Second Office Action dated Jul. 21, 2022, in corresponding Chinese Application No. 201911330633.8, 14 pages.
(Continued)

*Primary Examiner* — Sarah W Aleman
*Assistant Examiner* — Mikail A Mannan
(74) *Attorney, Agent, or Firm* — Maier & Maier, PLLC

(57) ABSTRACT

An occluder, an occluding system, and a conveying device are provided. The occluder includes an occluding frame. The occluding frame includes a first occluding unit, a middle portion occluding unit, a second occluding unit, and waist portions. Both ends of the middle portion occluding unit are connected to the first occluding unit and the second occluding unit, respectively, by the waist portions. A fixing member is sleeved on each waist portion. A channel is formed at a middle portion of each fixing member. The occluding frame (Continued)

has an inner cavity. A first opening is formed on the first occluding unit. A second opening is formed on the second occluding unit. The first opening, the channel, the inner cavity, and the second opening are communicated to form a path. A locking member can be omitted in the occluder.

19 Claims, 13 Drawing Sheets

(58) Field of Classification Search
CPC .......... A61B 2017/00004; A61B 2017/00867; A61B 2017/00876; A61B 2017/1205; A61B 2017/12095; A61B 17/12031
See application file for complete search history.

(56) References Cited

U.S. PATENT DOCUMENTS

| | | | |
|---|---|---|---|
| 2005/0267523 | A1 | 12/2005 | Devellian et al. |
| 2012/0316602 | A1 | 12/2012 | Chanduszko et al. |
| 2017/0290575 | A1* | 10/2017 | Sato ............... A61B 17/064 |
| 2019/0298382 | A1* | 10/2019 | Fung ............... A61B 17/12122 |

FOREIGN PATENT DOCUMENTS

| | | |
|---|---|---|
| CN | 204971420 U | 1/2016 |
| CN | 101687088 B | 9/2016 |
| CN | 106308867 A | 1/2017 |
| CN | 106983528 A | 7/2017 |
| CN | 206777355 U | 12/2017 |
| CN | 208447659 U | 2/2019 |
| CN | 109567891 A | 4/2019 |
| CN | 109247959 A | 12/2019 |
| CN | 209751119 U | 12/2019 |

OTHER PUBLICATIONS

Second Office Action dated Sep. 30 2022, in corresponding Chinese Application No. 201911329002.4, 35 pages.
Second Office Action dated Nov. 11, 2022, in corresponding Chinese Application No. 201911330630.4, 18 pages.
International Search Report dated Nov. 3, 2020, in corresponding to International Application No. PCT/CN2020/104523; 9 pages (with English Translation).
First Office Action dated Jan. 10, 2022, corresponding to Chinese Application No. 201911329002.4; 21 pages (with English Translation).
First Office Action dated Mar. 29, 2022, corresponding to Chinese Application No. 201911330630.4; 7 pages.
First Office Action dated Oct. 11, 2021, corresponding to Chinese Application No. 201911330633.8; 12 pages (with English Translation).
Notification to Grant Patent dated Oct. 19, 2022, in corresponding Chinese Application No. 201911330633.8, 3 pages.
Third Office Action dated Jan. 28, 2023, in corresponding Chinese Application No. 201911330630.4, 14 pages.
Examination Report dated Nov. 14, 2022, in corresponding Indian Application No. 202217035550, 6 pages.

* cited by examiner

OCCLUDER, OCCLUDING SYSTEM AND CONVEYING DEVICE

FIELD

The disclosure relates to the field of interventional medical instruments, and in particular, to an occluder, an occluding system and a conveying device.

BACKGROUND

This section provides background information related to the disclosure only and is not necessarily prior art.

Percutaneous interventional therapy is a disease treatment means that is developing very rapidly in recent years and is applied to more and more extensive fields. Transcatheter interventional therapy may be used to place instruments and/or drugs into the heart, arteriovenous vessels, and other parts of a human body. The instruments may be a cardiac occluder, a vascular occluder, a vascular filter, etc.

The traditional instruments such as the cardiac occluder or the vascular occluder are generally made of shape memory alloy materials, which have good elasticity, can return to an original shape after release, and can better fit tissues at defect sites. However, current memory alloy materials are generally materials that cannot be corroded or degraded by organisms. When endothelialization is completed to achieve complete occlusion, an occluder made of the memory alloy materials will be permanently retained in the body and may have long-term clinical risks.

For an occluder made of absorbable high-molecular materials or other implantable instruments, although the high-molecular materials can be degraded in the body, the occluder can be gradually degraded and degradation products will not remain in the organisms after being absorbed by the body. However, the high-molecular materials are relatively soft and difficult to form and have worse mesh stability than occluders made of alloy materials. Prior to conveying, it is necessary to axially stretch the occluder in order to load it into a conveying sheath, and after conveying the occluder into the body, it is necessary to keep the occluder axially stretched before the occluder can be accurately positioned. In order to avoid damaging the occluder, it is necessary to avoid damaging the occluder frame by excessively pulling the occluder when stretching. In order to solve this problem, an existing occluder is provided with an axially extending locking member in an occluding frame. During loading, a force is applied to the locking member such that the occluder is pushed straight to achieve axial stretching of the occluder. In order to achieve the above-described function, the locking member is required to have a certain stiffness and length to assist in straightening the occluder to achieve axial stretching.

However, the rigid locking member extends axially in the occluding frame, which increases the rigidity of the occluder after stretching to a certain extent, increases the difficulty of conveying, and does not facilitate passage through curved vessels. Moreover, in view of a vascular occluder, the presence of the locking member may affect the adjustment of the length of the vascular occluder due to a large difference in the length of the diseased vessel.

SUMMARY

Based on this, it is desired to provide an occluder in which a locking member can be omitted, and an occluding system. Further, a conveying device is provided.

An occluder includes an occluding frame. The occluding frame includes a first occluding unit, a middle portion occluding unit, a second occluding unit, and waist portions. Both ends of the middle portion occluding unit are connected to the first occluding unit and the second occluding unit, respectively, by the waist portions. A fixing member is sleeved on each waist portion. A channel is formed at a middle portion of each fixing member. The occluding frame has an inner cavity. A first opening is formed on the first occluding unit. A second opening is formed on the second occluding unit. The first opening, the channel, the inner cavity, and the second opening are communicated to form a path.

In one embodiment, the fixing member is a sleeve formed of a high-molecular material or an annular structure formed by winding a high-molecular wire around the periphery of the waist portion.

In one embodiment, there is at least one middle portion occluding unit, there are at least two waist portions, when there is more than one middle portion occluding unit, there are more than two waist portions, and the more than one middle portion occluding unit and the more than two waist portions are alternately arranged in an axial direction.

In one embodiment, an axial length of the middle portion occluding unit is greater than that of the first occluding unit and the second occluding unit.

In one embodiment, the occluder further includes a first occluding head and a second occluding head. The first occluding head and the second occluding head are arranged on the first occluding unit and the second occluding unit, respectively. The first occluding head is provided with a first through hole. The second occluding head is provided with a second through hole. The first through hole is communicated with the first opening. The second through hole is communicated with the second opening.

An occluding system includes a conveying device and the above-described occluder. The conveying device includes an adjusting member that is slidable along the path until a distal end of the adjusting member extends out of the inner cavity, and the distal end of the adjusting member is abuttable against the first occluding unit.

In one embodiment, one end of the adjusting member has a pre-bending portion in a natural state. When the adjusting member is slidable along the path until the pre-bending portion is located outside the occluding frame, the pre-bending portion returns to a bending state and is abuttable against the first occluding unit.

In one embodiment, the pre-bending portion is an arc-shaped rod or an arc-shaped wire at an angle of 40-90°.

In one embodiment, the conveying device further includes a pushing member having an inner cavity. The pushing member is slidable along the path until a distal end of the pushing member abuts against the first occluding head, and the adjusting member slidably passes through the pushing member.

In one embodiment, the pushing member has an outer diameter that is 0.1-4 mm less than a radial width of the channel.

In one embodiment, when the first through hole is a trapezoidal hole, the distal end of the pushing member is trapezoidal, and when the first through hole is a stepped hole, the distal end of the pushing member is stepped.

In one embodiment, the first through hole is a trapezoidal or stepped hole. The conveying device further includes a transition member that is sleeved on the distal end of the pushing member and matched with the trapezoidal or stepped hole in shape such that the transition member abuts against the first occluding head when the pushing member is slidable along the path until the distal end of the pushing member extends into the trapezoidal or stepped hole.

In one embodiment, the conveying device further includes an interlocking mechanism for keeping the adjusting member and the pushing member locked.

A conveying device for conveying an implantable instrument includes:
an adjusting member, having a distal end and a proximal end, the distal end of the adjusting member having a pre-bending portion in a natural state;
an operating handle, the proximal end of the adjusting member being connected to the operating handle; and
an adjusting member control member, arranged on the operating handle and connected to the proximal end of the adjusting member for controlling the displacement of the adjusting member such that the pre-bending portion of the adjusting member abuts against the implantable instrument to achieve forming of the implantable instrument.

In one embodiment, the conveying device further includes a pushing member and a pushing member control member. The pushing member control member is arranged on the operating handle. A proximal end of the pushing member is connected to the pushing member control member. The pushing member control member is configured to control the displacement of the pushing member. Moreover, the pushing member has an inner cavity, and the adjusting member passes through the pushing member.

In one embodiment, the conveying device further includes an interlocking mechanism that is arranged on the operating handle for keeping the adjusting member and the pushing member detachably locked.

In one embodiment, the interlocking mechanism includes at least two magnetic components that are arranged on the adjusting control member and the pushing control member, respectively. The number of magnetic components on the adjusting control member and the number of magnetic components of the pushing control member are equal or unequal, the magnetic components on the adjusting control member and the magnetic components of the pushing control member are arranged oppositely, and opposite parts of the magnetic components on the adjusting control member and the magnetic components of the pushing control member have different polarities.

In one embodiment, the operating handle includes a housing and an upper cover detachably connected to the housing. The housing and the upper cover form a first track, a second track parallel to the first track is arranged in the housing, and the adjusting control member and the pushing control member are slidably arranged on the second track. The adjusting control member includes a first operating portion that is located outside the operating handle, the pushing control member includes a second operating portion that is located outside the operating handle, and the adjusting member control member and the pushing control member are axially displaceable along the first track and the second track by operating the first operating portion and the second operating portion.

In one embodiment, the interlocking mechanism includes a locking member that is located outside the operating handle and detachably connected to the first operating portion and the second operating portion for locking the adjusting control member and the pushing control member.

In one embodiment, the conveying device further includes a transition member that is sleeved on the distal end of the pushing member and provided with an opening communicated with the inner cavity of the pushing member.

The inner cavity, the first opening, the second opening, and the channel of the above-described occluder together form a path. During loading, the pushing member of the conveying device enters the path formed by the inner cavity, the first opening, the second opening, and the channel together and is displaced until the distal end of the pushing member abuts against the occluder to push the occluder straight, so as to achieve axial stretching. By sleeving the fixing member on the waist portion, the fixing member further fixes a path of the pushing member moving inside the occluding frame, which is beneficial to avoid damage to the occluding frame caused by the fact that the pushing member deviates from a preset direction to hit the occluding frame. Moreover, the position of the occluder can be adjusted by keeping the pushing member abutting against the occluder to maintain an axial stretching state of the occluder due to the restriction of the fixing member. Therefore, with the omission of the locking member, axial stretching of the occluder can also be conveniently achieved to load the occluder into the conveying sheath and maintain the axial stretching state of the occluder, thereby facilitating adjustment of the position of the occluder.

DETAILED DESCRIPTION OF THE EMBODIMENTS

In order that the above objects, features, and advantages of the embodiments can be more readily understood, implementations of the embodiments will be described below in detail with reference to the accompanying drawings. In the following description, numerous specific details are set forth in order to provide a thorough understanding of the embodiments. The embodiments may, however, be embodied in many different forms than those herein set forth, and such modifications as would occur to those skilled in the art may be made without departing from the spirit and scope of the embodiments.

Unless defined otherwise, all technical and scientific terms used herein have the same meaning as commonly understood by those skilled in the art to which the embodiments belongs. The terms used in the description of the disclosure are only for the purpose of describing embodiments, but are not intended as limiting.

In the field of interventional medical instruments, an end that is further away from an operator during a surgical process is defined as a "distal end", and an end that is closer to the operator during the surgical process is defined as a "proximal end". An "axial direction" refers to a direction parallel to a line connecting a distal center and a proximal center of a medical instrument, and a "radial direction" refers to a direction perpendicular to the above-described axial direction.

Figure 1:
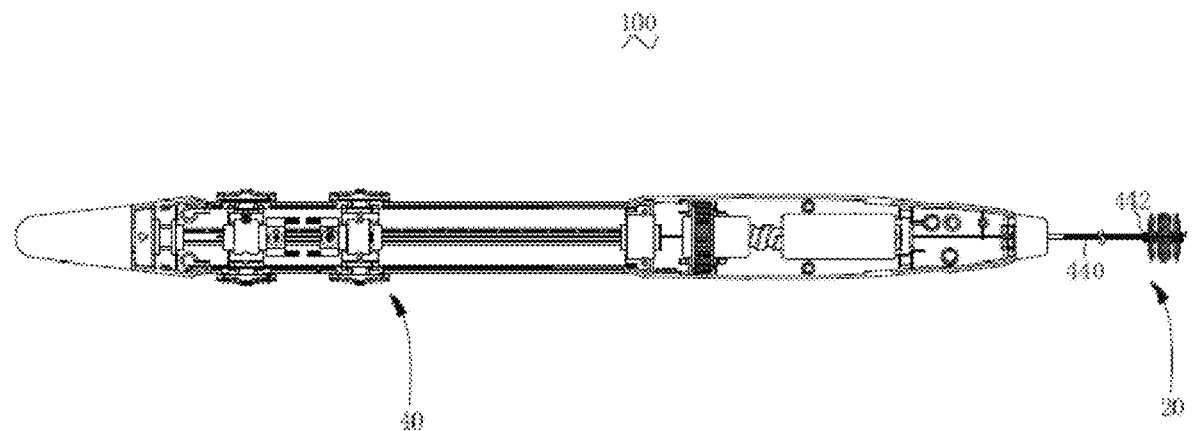
FIG. 1 is a schematic structural diagram of an occluding system according to an implementation.

Referring to FIG. 1, an occluding system 100 of an implementation includes an occluder 20 and a conveying device 40. The occluder 20 is detachably connected to the conveying device 40. After the occluder 20 is pushed to a lesion site in an organism through the conveying device 40, the occluder 20 is disconnected from the conveying device 40, and the conveying device 40 is withdrawn from the organism to complete an implanting surgery.

Figure 2:
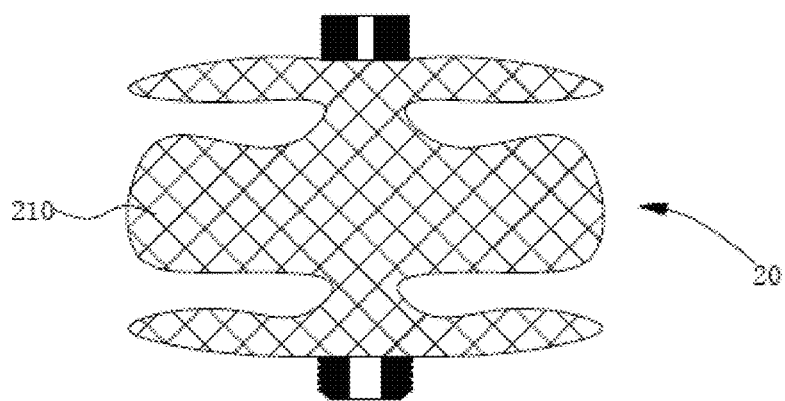
FIG. 2 is a schematic structural diagram of an occluder according to an implementation.

Referring to FIG. 2, in an implementation, the occluder 20 includes an occluding frame 210. The occluding frame 210 is a mesh structure formed by weaving a high-molecular material or by 3D printing or in other ways.

In an implementation, the occluding frame 210 adopts at least one material selected from the group consisting of L-polylactic acid, racemic polylactic acid, polyglycolic acid, poly(lactic-co-glycolic acid), polyhydroxyalkanoate, polydioxanone, polycaprolactone, poly(gluconic acid), polyhydroxybutyrate, polyanhydride, polyphosphoester, polyglycolic acid, and polydioxanone.

In an implementation, the material of the occluding frame 210 is a copolymer formed by copolymerizing at least two of monomers forming L-polylactic acid, racemic polylactic acid, polyglycolic acid, poly(lactic-co-glycolic acid), polyhydroxyalkanoate, polydioxanone, polycaprolactone, poly(gluconic acid), polyhydroxybutyrate, polyanhydride, polyphosphoester, polyglycolic acid, and polydioxanone.

Figure 3:
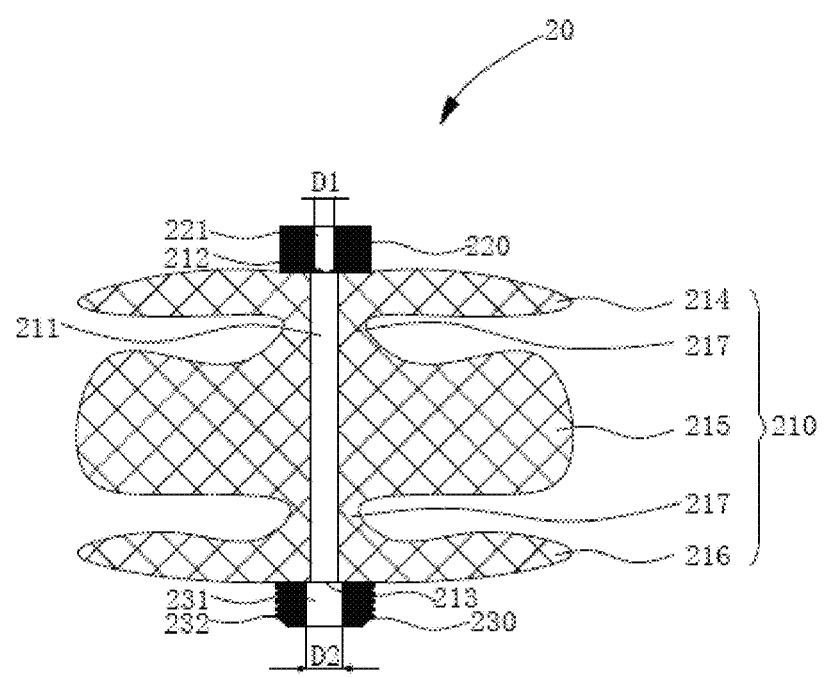
FIG. 3 is a schematic structural diagram of an occluder according to an implementation.

Referring to FIG. 3, the occluding frame 210 has an inner cavity 211 (the inner cavity 211 is located inside the occluding frame 210, and for convenience of illustration, FIG. 3 generally depicts the inner cavity 211 to show a position relationship between the inner cavity 211 and first and second openings 212 and 213), and the occluding frame 210 has the first opening 212 and the second opening 213, which are opposite to each other. The first opening 212 and the second opening 213 are respectively located at a distal end and a proximal end of the occluding frame 210, and the inner cavity 211, the first opening 212 and the second opening 213 are communicated to form a path. In an implementation, a plurality of woven wires are woven to form the occluding frame 210, and both free ends of the plurality of woven wires are respectively closed up to form the first opening 212 and the second opening 213. In an implementation, both free ends of the plurality of woven wires are respectively closed up with an annular close-up member.

In an implementation, the occluder 20 further includes a first occluding head 220 and a second occluding head 230. The first occluding head 220 and the second occluding head 230 are respectively arranged at two opposite ends of the occluding frame 210. The first occluding head 220 is provided with a first through hole 221, and the first through hole 221 is communicated with the first opening 212. The second occluding head 230 is provided with a second through hole 231, and the second through hole 231 is communicated with the second opening 213.

In an implementation, the first occluding head 220 and the second occluding head 230 are respectively used to close up both free ends of the plurality of woven wires, and the first opening 212 communicated with the first through hole 221 and the second opening 213 communicated with the second through hole 231 are formed. For example, the first occluding head 220 and the second occluding head 230 respectively form a receiving groove, both free ends of the plurality of woven wires are respectively inserted and fixed in the receiving groove of the first occluding head 220 and the receiving groove of the second occluding head 230, and the first opening 212 communicated with the first through hole 221 and the second opening 213 communicated with the second through hole 231 are formed.

In an implementation, both the first occluding head 220 and the second occluding head 230 are located outside the occluding frame 210 in such a way to facilitate processing.

In an implementation, both the first occluding head 220 and the second occluding head 230 are located inside the occluding frame 210 in such a way to help avoid thrombus formation and to help avoid scratching of tissue by the first occluding head 220 and/or the second occluding head 230 due to improper operation during release.

In an implementation, the first occluding head 220 is arranged inside the occluding frame 210, and the second occluding head 230 is arranged outside the occluding frame 210, so as to avoid thrombus formation and to avoid scratching of tissues by the first occluding head 220, while facilitating detachable connection between the conveying device 40 and the second occluding head 230.

In an implementation, external threads 232 are formed on an outer wall of the second occluding head 230 to facilitate connection with the conveying device 40.

In an implementation, the first occluding head 220 may be omitted. In another implementation, both the first occluding head 220 and the second occluding head 230 may be omitted when the proximal end of the occluding frame 210 contains other components that may be detachably connected to the conveying device 40.

In an implementation, the materials of the first occluding head 220 and the second occluding head 230 are degradable high-molecular materials. The materials of the first occluding head 220 and the second occluding head 230 may be the same as or different from the material of the occluding frame 210.

The first occluding head 220 and the second occluding head 230 are substantially rigid high-molecular tubes. Since the occluding frame 210 is relatively flexible, the first occluding head 220 and the second occluding head 230 are provided to facilitate the loading, pushing, releasing and shaping of the occluding device 20.

The first through hole 221 has an aperture D1, and the second through hole 231 has an aperture D2.

With continued reference to FIG. 3, the occluding frame 210 includes a first occluding unit 214, a middle portion occluding unit 215 and a second occluding unit 216. Two opposite ends of the middle portion occluding unit 215 are respectively connected to the first occluding unit 214 and the second occluding unit 216. The first opening 212 is formed on the first occluding unit 214, and the second opening 213 is formed on the second occluding unit 216.

In an implementation, the occluding frame 210 further includes waist portions 217. There are two waist portions 217. Both ends of one of the waist portions 217 are respectively connected to the first occluding unit 214 and the middle portion occluding unit 215, and both ends of the other waist portion 217 are respectively connected to the middle portion occluding unit 215 and the second occluding unit 216. A radial dimension of the waist portions 217 is smaller than that of the first occluding unit 214, the middle portion occluding unit 215 and the second occluding unit 216.

In an implementation, an axial length of the middle portion occluding unit 215 is greater than that of the first occluding unit 214 and the second occluding unit 216, so that after implantation, the contact area of the occluder 20 with a lesion site (e.g. a vessel wall) is larger, which is beneficial to improve anchoring of the occluder 20 at the lesion site.

In an implementation, the first occluding unit 214 and the second occluding unit 216 are both disc-shaped, the middle portion occluding unit 215 is cylindrical, and the cylindrical middle portion occluding unit 215 is connected to the disc-shaped first occluding unit 214 and second occluding unit 216 through the waist portions 217 having a smaller radial dimension. On the one hand, the combination of the cylindrical middle portion occluding unit 215 and the disc-shaped first occluding unit 214 and second occluding unit 216 ensures the contact area with the lesion site (e.g. the vessel wall). On the other hand, the middle portion occluding unit 215 is connected to both the first occluding unit 214 and the second occluding unit 216 through the waist portions 217 having a smaller radial dimension, so that an angle between the first occluding unit 214 and the middle portion occluding unit 215 and an angle between the middle portion occluding unit 215 and the second occluding unit 216 can be adjusted, which is beneficial to adapt the occluder 20 to different forms of lesion sites so as to adapt to different individuals. On the other hand, the above-described connection mode makes the occluder 20 after axial stretching more flexible, which facilitates smooth conveying to the lesion site through curved vessels.

In other implementations, at least one of the two waist portions 217 may be omitted.

Figure 4:
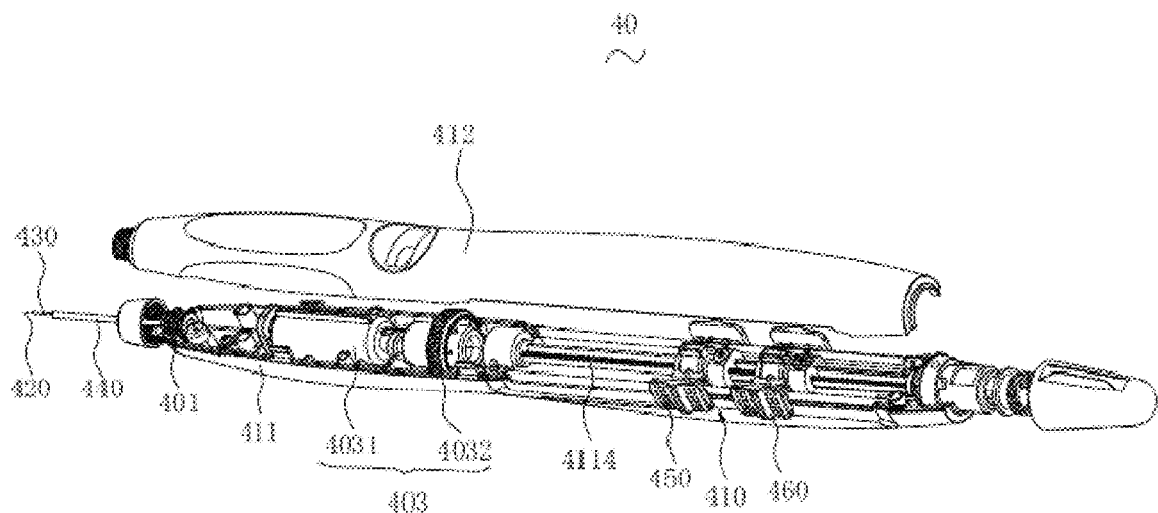
FIG. 4 is an exploded schematic diagram of a conveying device according to an implementation.

Referring to FIG. 4, the conveying device 40 includes an operating handle 410, an adjusting member 420, a pushing member 430, and a conveying member 440. The adjusting member 420 has a distal end and a proximal end, and the proximal end of the adjusting member 420 is connected to the operating handle 410. The pushing member 430 has a distal end and a proximal end, and the proximal end of the pushing member 430 is connected to the operating handle 410. The conveying member 440 has a distal end and a proximal end, and the proximal end of the conveying member 440 is connected to the operating handle 410. The loading, pushing, releasing and shaping of the occluder 20 is achieved by controlling the displacement of the adjusting member 420, the pushing member 430 and the conveying member 440 by operation on the operating handle 410.

The operating handle 410 includes a housing 411 and an upper cover 412. The housing 411 and the upper cover 412 are detachably connected. When the housing 411 and the upper cover 412 are connected, the housing 411 and the upper cover 412 define an accommodating cavity.

Figure 5:
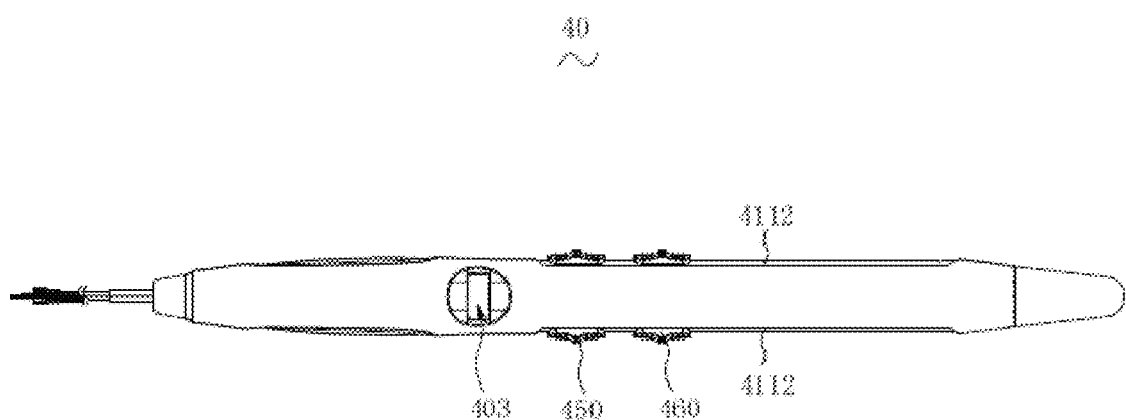
FIG. 5 is a schematic diagram of an external structure of a conveying device according to an implementation.

An edge of the housing 411 is provided with a first groove, an edge of the upper cover 412 is provided with a second groove, and the first groove and the second groove constitute a first track 4112, as shown in FIG. 5. In an implementation, there are two first grooves and two second grooves, which form two first tracks 4112 opposite and parallel to each other.

Figure 6:
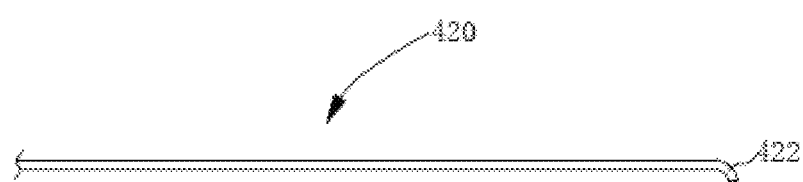
FIG. 6 is a schematic structural diagram of an adjusting member according to an implementation.

Referring to FIG. 6, the adjusting member 420 is an elongated rod member. For example, the adjusting member 420 is an elongated, rigid metal rod or wire.

In an implementation, the material of the adjusting member 420 is a shape memory metal material or a shape memory alloy material. In an implementation, the material of the adjusting member 420 is a nickel-titanium alloy.

In a natural state, the distal end of the adjusting member 420 (i.e. an end away from the operating handle 410) has a pre-bending portion 422. When the adjusting member 420 is bound, e.g. in a lumen structure, the pre-bending portion 422 is substantially straightened. When the binding disappears, the pre-bending portion 422 returns to the natural state, i.e. a bending form.

The pre-bending portion 422 is an arc-shaped rod or an arc-shaped wire. One end of the elongated shape memory metal rod or wire or the shape memory alloy rod or wire is bent and shaped to obtain the adjusting member 420 having the pre-bending portion 422.

Figure 7:
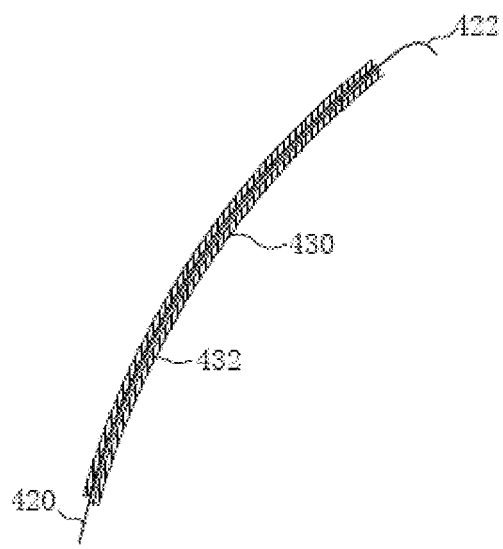
FIG. 7 is a schematic diagram of a position relationship between an adjusting member and a pushing member according to an implementation.
Figure 8A:
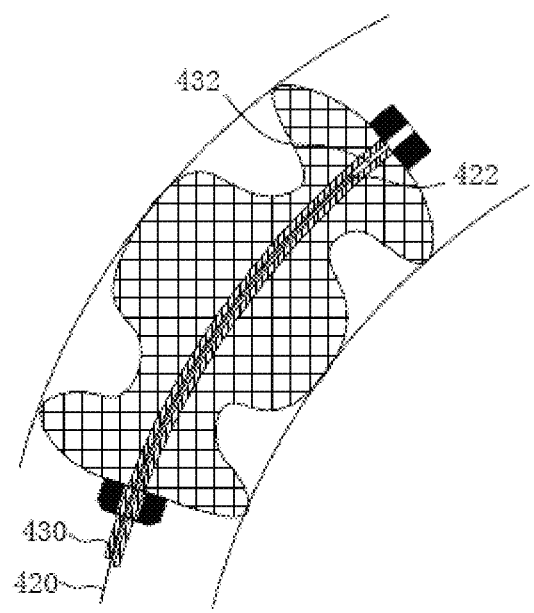
FIG. 8a is a schematic diagram of a form of an occluder implanted in a blood vessel according to an implementation.

Referring to FIG. 7, the pushing member 430 is a hollow tube member. The pushing member 430 has an inner cavity 432 extending axially from the distal end to the proximal end. The adjusting member 420 is slidably received in the inner cavity 432 of the pushing member 430, i.e. the adjusting member 420 slidably passes through the pushing member 430. When the pre-bending portion 422 of the adjusting member 420 is located in the inner cavity 432, the pre-bending portion 422 is substantially straightened, as shown in FIG. 8a. When the pre-bending portion 422 of the adjusting member 420 is located outside the inner cavity 432, the pre-bending portion 422 returns to a natural bending state, as shown in FIGS. 7 and 8b.

Figure 8B:
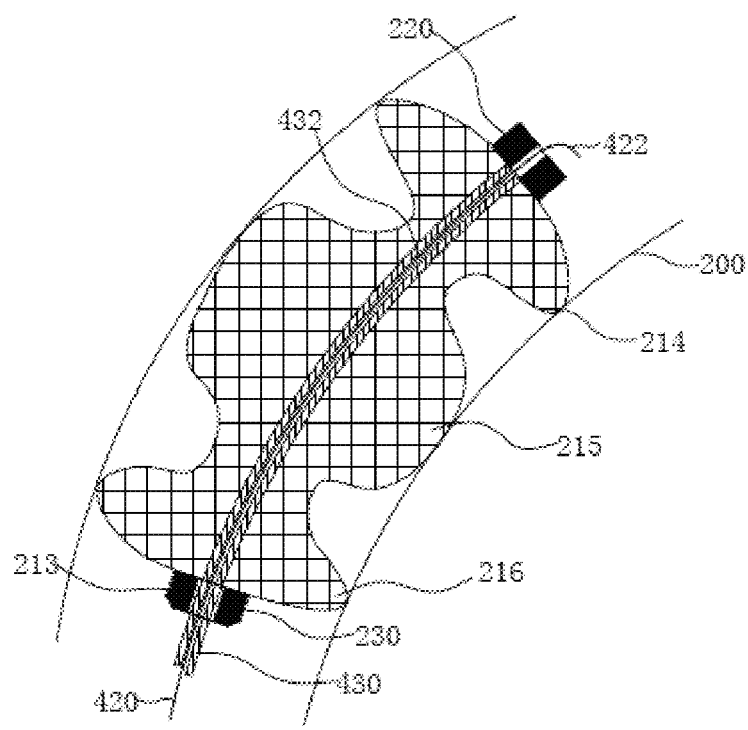
FIG. 8b is a schematic diagram of a form of an occluder implanted in a blood vessel according to an implementation.

Referring to FIGS. 3 and 8b together, by operating the operating handle 410, such that the pushing member 430 enters a path formed by the inner cavity 211, the first opening 212 and the second opening 213 of the occluding frame 210 from the second through hole 213 of the second occluding head 230, and the pushing member 430 may slide from the second through hole 213 until the distal end of the pushing member 430 abuts against the first occluding head 220.

Figure 9:
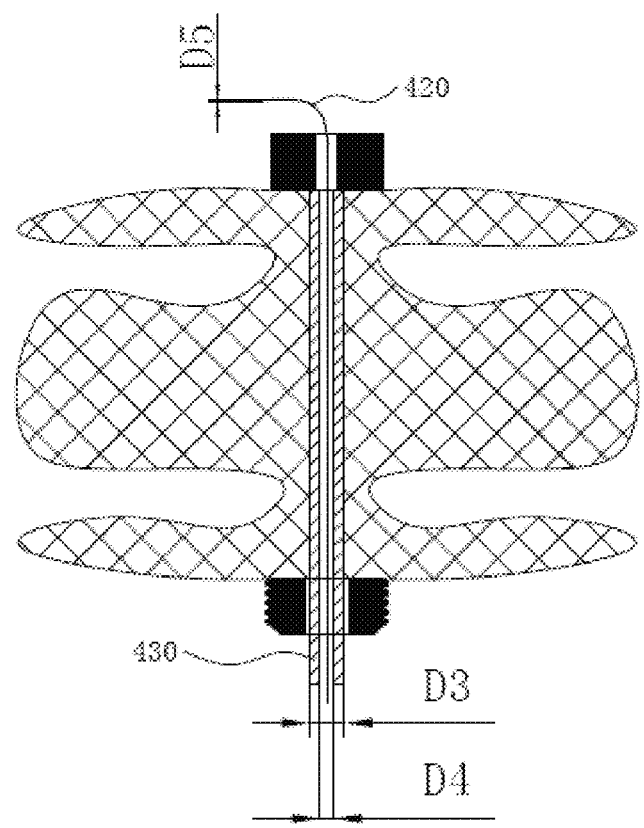
FIG. 9 is a schematic diagram of a position relationship among an occluder, an adjusting member and a pushing member according to an implementation.

Referring to FIG. 9, the pushing member 430 has an outer diameter D3 and an inner diameter D4. The outer diameter of the adjusting member 420 is D5. Referring to FIGS. 3 and 9, D2>D3>D1>D4>D5, so that the occluder 20, the adjusting member 420 and the pushing member 430 cooperate to achieve the loading, pushing, releasing and shaping of the occluder 20.

It should be noted that when the first through hole 221 and the second through hole 223 are irregularly-shaped through holes, the aperture D1 of the first through hole 221 refers to an aperture at a minimum position. The aperture D2 of the second through hole 223 also refers to the aperture at the minimum position.

Returning to FIG. 1, the conveying member 440 is a hollow tube member. In an implementation, the conveying member 440 is a hollow stainless steel spring tube. In an implementation, the conveying member 440 is a hollow nickel-titanium cable.

In an implementation, the distal end of the conveying member 440 is provided with a connecting portion 442, and an inner wall of the connecting portion 442 is provided with internal threads (not shown in FIG. 1), which fit the external threads 232 of the second occluding head 230 such that the second occluding head 230 is detachably connected to the conveying member 440.

Referring again to FIG. 4, the proximal end of the conveying member 440 extends into the operating handle 410 and is fixedly connected to the operating handle 410 through the fixing member 401. The fixing member 401 is arranged in the housing 411. The pushing member 430 slidably passes through the conveying member 440. The adjusting member 420 slidably passes through the pushing member 430.

The conveying device 40 further includes an adjusting control member 450 and a pushing control member 460. The adjusting control member 450 is partially located in the accommodating cavity defined by the housing 411 and the upper cover 412, is arranged on the housing 411, and is partially located outside the operating handle 410. The pushing control member 460 is partially located in the accommodating cavity defined by the housing 411 and the upper cover 412, is arranged on the housing 411, and is partially located outside the operating handle 410. Referring to FIG. 5 together, the adjusting control member 450 includes a first operating portion 452. The first operating portion 452 is a portion of the adjusting control member 450 outside the operating handle 410. The pushing control member 460 includes a second operating portion 462. The second operating portion 462 is a portion of the pushing control member 460 outside the operating handle 410.

A second track 4114 is arranged in the housing 411, and the first track 4112 and the second track 4114 are parallel. The first operating portion 452 and the second operating portion 462 are operable to axially translate the adjusting control member 450 and the pushing control member 460 along the first track 4112 and the second track 4114. When there are two first tracks 4112, there are two first operating portions 452 and two second operating portions 462 correspondingly, so as to facilitate the operation.

The proximal end of the adjusting member 420 is connected to the adjusting control member 450 to control the displacement of the adjusting member 420 by operating the adjusting control member 450. The proximal end of the pushing member 430 is connected to the pushing control member 460 to control the displacement of the pushing member 430 by operating the pushing control member 460.

In an implementation, the conveying device 40 further includes an interlocking mechanism for keeping the adjusting member 420 and the pushing member 430 detachably locked.

Figure 10:
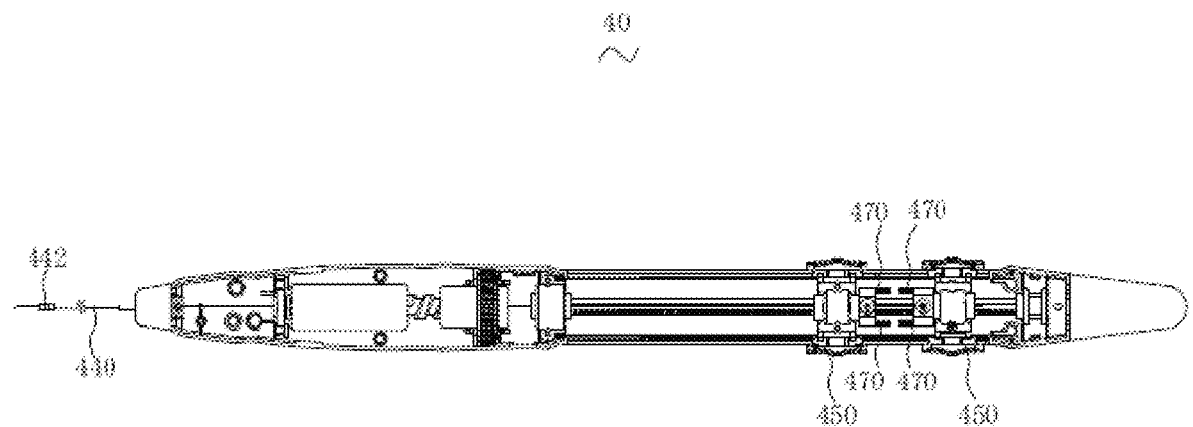
FIG. 10 is a schematic diagram of an internal structure of a conveying device according to an implementation.

In an implementation, referring to FIG. 10, the interlocking mechanism includes a magnetic component 470. In an implementation, the interlocking mechanism includes at least two magnetic components 470. When there are two magnetic components 470, one of the magnetic components 470 is arranged on the adjusting control member 450, the other magnetic component 470 is arranged on the pushing control member 460, and the two magnetic components 470 are opposite to each other. The opposite portions of the two magnetic components 470 have different polarities, so that the two magnetic components 470 can attract each other to adsorb the adjusting control member 450 and the pushing control member 460 together to keep the adjusting member 420 and the pushing member 430 locked. In a locked state, the adjusting member 420 and the pushing member 430 cannot be relatively displaced. When the adjusting member 420 and the pushing member 430 need to be relatively displaced, a force greater than an adsorption force of the magnetic components 470 may be applied to the adjusting control member 450 or the pushing control member 460.

In an implementation, when there are more than two magnetic components 470, the magnetic components 470 are arranged in the same way as described above, so that the opposite attraction should be satisfied. The number of magnetic components 470 on the adjusting control member 450 and the pushing control member 460 may be equal or different, and the detachable connection can be achieved only when the opposite attraction is satisfied.

By providing the magnetic components 470, it is more convenient to lock and unlock the adjusting control member 450 and the pushing control member 460, and the structure inside the operating handle 410 is more compact.

The material of the magnetic components 470 is another magnetic material such as a magnet.

Figure 11:
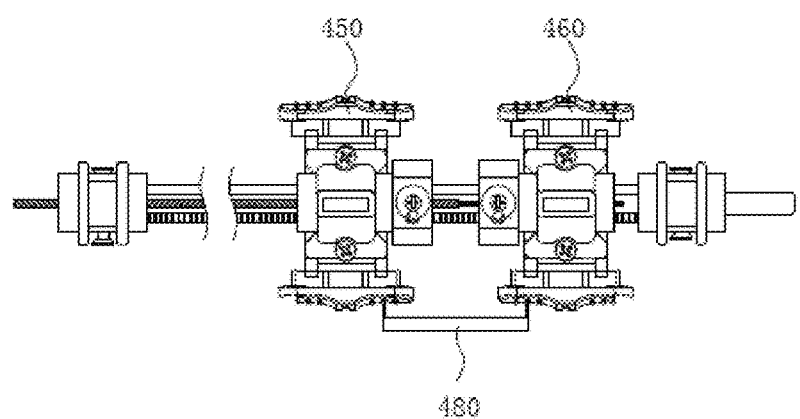
FIG. 11 is a schematic diagram of a connection relationship between an adjusting member, a pushing member and an interlocking mechanism according to an implementation.
Figure 12:
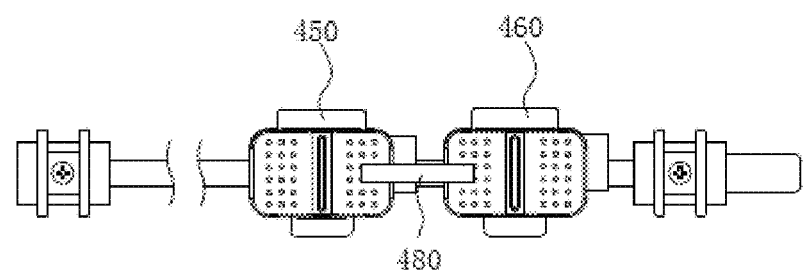
FIG. 12 is a schematic diagram of a connection relationship between an adjusting member, a pushing member and an interlocking mechanism according to an implementation.

In an implementation, the magnetic components 470 are omitted. Referring to FIGS. 11 and 12 together, the interlocking mechanism includes a locking member 480. The locking member 480 is arranged outside the operating handle 410, the locking member 480 is detachably connected to the first operating portion 452 of the adjusting control member 450, and the locking member 480 is detachably connected to the second operating portion 462 of the pushing control member 460. When the locking member 480 is simultaneously connected to the adjusting control member 450 and the pushing control member 460, the locking member 480 integrally connects the adjusting control member 450 and the pushing control member 460, so that the adjusting control member 450 and the pushing control member 460 cannot be relatively displaced, thereby achieving locking of the adjusting member 420 and the pushing member 430. When the adjusting member 420 and the pushing member 430 need to be relatively displaced, the adjusting control member 450 or the pushing control member 460 may be operated to relatively displace the adjusting member 420 and the pushing member 430 upon unlocking of the locking member 480.

It should be noted that the detachable connection between the locking member 480 and the adjusting control member 450 and the detachable connection between the locking member 480 and the pushing control member 460 may be in a manner known to those skilled in the art, for example, a buckle connection, a hinge connection, etc.

When the adjusting member 420 and the pushing member 430 need to be locked, the locking member 480 is connected to both the adjusting member 420 and the pushing member 430. When the adjusting member 420 and the pushing member 430 need to be unlocked, it is sufficient to unlock the connection of the locking member 480 to at least one of the adjusting member and the pushing member. The locking and unlocking occur outside the operating handle 410, making the operation more reliable. Even if an improper force is applied, the inside of the operating handle 410 will not be affected, thereby avoiding undesirable phenomena of displacement of the occluder 20, etc.

Figure 13:
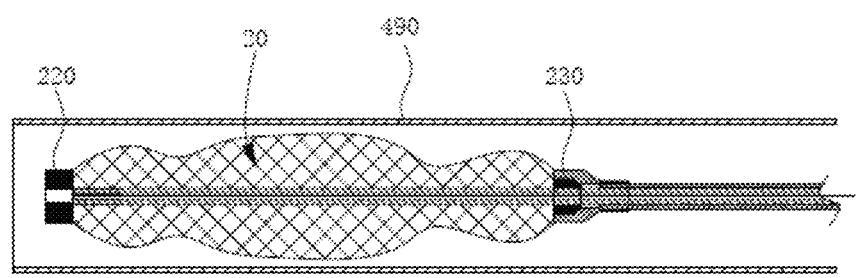
FIG. 13 is a schematic diagram of a loading state of an occluder according to an implementation.
Figure 14:
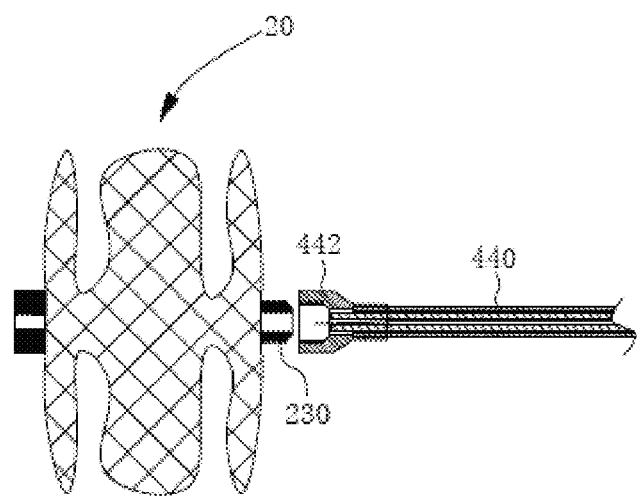
FIG. 14 is a schematic diagram of connection between an occluder and a conveying device according to an implementation.
Figure 15:
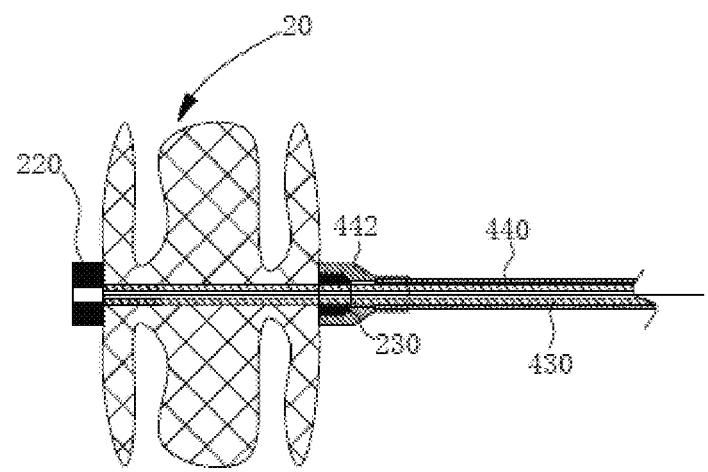
FIG. 15 is a schematic diagram of connection between an occluder and a conveying device according to an implementation.

When an implanting surgery is to be performed, the occluder 20 should first be reloaded into a conveying sheath 490 (see FIG. 13). First, the conveying member 440 (internally inserted with the adjusting member 420 and the pushing member 430) passes through the conveying sheath 490, and the distal end of the conveying member 440 extends from the conveying sheath 490. Further, the connecting portion 442 of the conveying member 440 is connected to the second occluding head 230 of the occluder 20 (as shown in FIGS. 14 and 15). Then, the adjusting control member 450 and the pushing control member 460 are in a locked state, so that the adjusting control member 450 and the pushing control member 460 axially translate distally together along the first track 4112 and the second track 4114, thereby driving the pushing member 430 to axially translate distally until the pushing member 430 enters the path formed by the inner cavity 211, the first opening 212 and the second opening 213 of the occluding frame 210 from the second occluding head 230, and to continue to translate until the distal end of the pushing member 430 abuts against the first occluding head 220. The pushing member 430 continues to translate distally by continuously operating the pushing control member 460, so that the occluder 20 becomes fully axially stretched when an axial distance between the first occluding head 220 and the second occluding head 230 is maximal. At this moment, the pushing control member 460 and the adjusting control member 450 still keep locked. The operating handle 410 is displaced proximally to pull the axially stretched occluder 20 into the inner cavity of the conveying sheath 490, as shown in FIG. 13.

Figure 16:
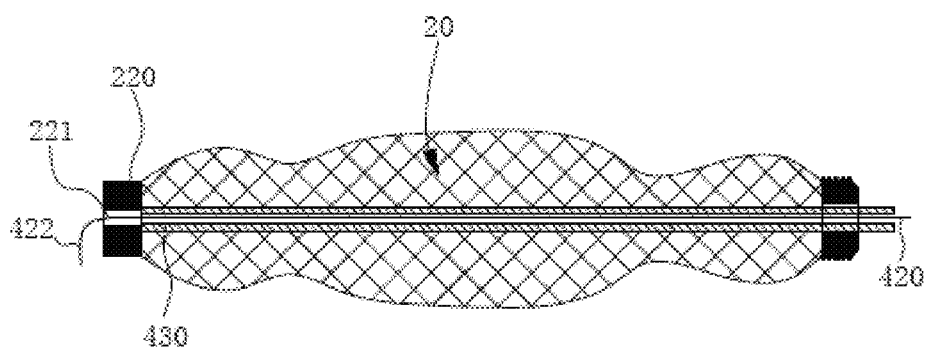
FIG. 16 is a schematic diagram of a state after an occluder exits from a conveying sheath according to an implementation.

After the conveying sheath 490 conveys the occluder 20 to the lesion site, the operating handle 410 is displaced distally to push the occluder 20 out of the conveying sheath 490. When the occluder 20 is pushed out of the conveying sheath 490, the distal end of the pushing member 430 still abuts against the first occluding head 220 at this moment, and the position of the pushing control member 460 is unchanged, so that the occluder 20 is still stretched, as shown in FIG. 16. Therefore, it is necessary to change the occluder 20 to an expanded state. The adjusting control member 450 and the pushing control member 460 are unlocked, so that the adjusting control member 450 is axially displaced distally to drive the adjusting member 420 to be axially displaced distally. Thus, the pre-bending portion 422 of the adjusting member 420 extends from the first through hole 221 of the first occluding head 220 to be displaced outside the occluder 20. The pre-bending portion 422 returns to a natural state, i.e. a bending state, as shown in FIG. 16. Further, the adjusting control member 450 and the pushing control member 460 are simultaneously operated to simultaneously axially displace the adjusting member 420 and the pushing member 460 proximally. Since the distal end of the adjusting member 420 is provided with the pre-bending portion 422, during the displacement of the adjusting member 420, the pre-bending portion 422 hooks the first occluding head 220, i.e. an inner side surface of the pre-bending portion 422 abuts against a distal end surface of the first occluding head 220, so that the length of the occluder 20 is reduced as the adjusting member 420 is displaced proximally. Even if the occluder 20 gradually returns to the expanded state, peripheral surfaces of the first occluding unit 214, the middle portion occluding unit 215 and the second occluding unit 216 of the occluder 20 abut against an inner wall of a blood vessel 200, as shown in FIG. 8b. When the occluder 20 returns to the expanded state, the interlocking mechanism is opened to unlock the adjusting control member 450 and the pushing control member 460. The adjusting member 420 slides proximally by continuously operating the adjusting control member 450, so that the distal end of the adjusting member 420 returns to the inner cavity 432 of the pushing member 430, as shown in FIG. 8a. The adjusting control member 450 and the pushing control member 460 are locked again to withdraw the adjusting member 420 and the pushing member 430 simultaneously, or the adjusting control member 450 and the pushing control member 460 are not locked to withdraw the adjusting member 420 and the pushing member 430 respectively, so as to complete the implanting surgery.

One end of the adjusting member 420 of the above-described occluding system 100 has the pre-bending portion 422. When the pre-bending portion 422 returns to a bending state and abuts against the occluder 20, the adjusting member 420 is pulled proximally in an axial direction, so that the pre-bending portion 422 drives the distal end of the occluder 20 to be displaced proximally, thereby returning the occluder 20 to the expanded state.

In an implementation, the aperture D1 of the first through hole 221 is within a size range of 0.3-0.85 mm, and the pre-bending portion 422 is within an angle range of 40-90° (referring to a central angle of a sector where the pre-bending portion 422 of the arc-shaped rod structure or arc-shaped wire is located). In this way, on the one hand, it is ensured that the pre-bending portion 422 has a sufficient contact area with the first occluding head 220 to facilitate the adjustment of the length of the occluder 20 and promote the occluder 20 to return to the expanded state, but it is also avoided that the pre-bending portion 422 is difficult to withdraw into the first occluding head 220 due to excessive bending of the pre-bending portion 422 with respect to the rest of the adjusting member 420. On the other hand, the size of the pre-bending portion 422 is matched with that of the first through hole 221, so that the pre-bending portion 422 can smoothly pass through the first through hole 221, and it is avoided that the size of the first occluding head 220 needs to be increased accordingly due to over-size of the first through hole 221, while it is avoided that the size of the first through hole 221 is excessively small, making it difficult for the pre-bending portion 422 to extend out of the first occluding head 220 and to withdraw into the first occluding head 220.

The above-described occluding system 100 achieves the loading, pushing, releasing and shaping of the occluder 20 by arranging the adjusting member 420 and the pushing member 430 cooperating with the occluder 20 in the conveying device 40. It is unnecessary to arrange additional components in the occluder 20 to achieve the loading, pushing, releasing and shaping of the occluder 20, so that the structure of the occluder 20 is relatively simple, the preparation process is simple, the preparation efficiency is high, and the preparation cost is low.

Moreover, the elimination of additional components in the occluder 20 advantageously reduces the radial dimension of the stretched occluder 20 so that the conveying sheath 490 having a smaller outer diameter may be used for conveying. Meanwhile, the stretched occluder 20 is more flexible to facilitate passage through a curved vessel path.

It should be noted that in the implementations shown in FIGS. 4, 5 and 10-12, the adjusting control member 450 is located at the distal end of the pushing control member 460. In other implementations, the positions of the adjusting control member 450 and the pushing control member 460 may be exchanged.

For a smaller-size occluder 20, the size of the first occluding head 220 is smaller and the aperture of the first through hole 221 is smaller correspondingly. The outer diameters of the adjusting member 420 and the pushing member 430 matching therewith are also smaller. It is thus difficult to load the occluder 20.

Moreover, in actual use, it is sometimes necessary to remove the occluder 20 from the conveying sheath 490 and reinstall it after the occluder 20 is loaded into the conveying sheath 490 in the above-described way, either before or after delivery. For example, prior to delivery, the occluder 20 needs to be removed from the conveying sheath 490 and reloaded due to inspection requirements. After delivery, e.g. during a surgery, the occluder 20 needs to be removed due to poor release and reloaded into the conveying sheath 490 prior to the implanting surgery.

During loading or reloading, it is not always possible to ensure that the pushing member 430 is exactly aligned with the first through hole 221 in the first occluding head 220 (axial central axes coincide), which causes difficulties in loading. When the axial central axis of the pushing member 430 is deviated from the axial central axis of the first through hole 221 to a high degree, the adjusting member 420 easily hits the first occluding head 220 in the process of sliding distally to extend the first occluding head 220, possibly damages the first occluding head 220 made of a high-molecular material, or causes a certain degree of damage to the adjusting member 420. Even if the pushing member 430 is exactly aligned with the first through hole 221, since the distal end of the adjusting member 420 is the pre-bending portion 422, the pre-bending portion 422 is straightened even when constrained, but it naturally has a tendency to return to the bending state, thus increasing the difficulty of passing through a straight hole (the first through hole 221), making it difficult for loading or reloading.

Figure 17:
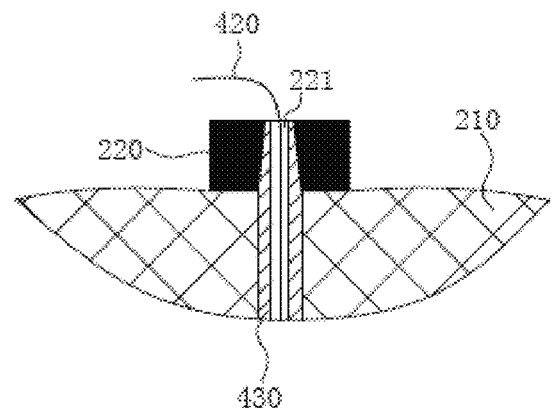
FIG. 17 is a schematic structural diagram of a first occluding head of an occluder and a pushing member according to an implementation.

In an implementation, referring to FIG. 17, the first through hole 221 is a trapezoidal hole having a larger sized end at the proximal end and a smaller sized end at the distal end. The distal end of the pushing member 430 is trapezoidal to match the shape of the distal end of the pushing member 430 with the shape of the first through hole 221. During the loading, pushing and releasing processes, the distal end of the pushing member 430 extends into the first through hole 221, and the distal end of the pushing member 430 abuts against a hole wall of the first through hole 221. In this way, it is advantageous to slow down or prevent the pushing member 430 and the first through hole 221 from deviating during the loading process and the surgical process, so that the adjusting member 420 smoothly extends out of the first occluding head 220 from the first through hole 221.

Figure 18:
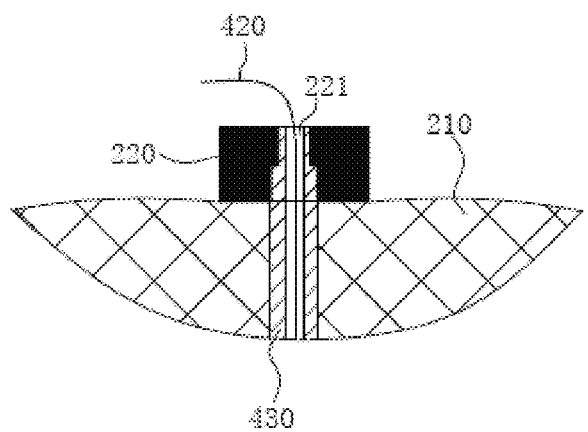
FIG. 18 is a schematic structural diagram of a first occluding head of an occluder and a pushing member according to another implementation.

In an implementation, referring to FIG. 18, the first through hole 221 is a stepped hole having a larger sized end at the proximal end and a smaller sized end at the distal end. A hole wall of the stepped hole has a step. The distal end of the pushing member 430 is stepped to match the shape of the distal end of the pushing member 430 with the shape of the first through hole 221. The distal end of the pushing member 430 also has a step. During the loading, pushing and releasing processes, the distal end of the pushing member 430 extends into the first through hole 221, and the step of the pushing member 430 abuts against the step of the first through hole 221. Thus, it is advantageous to keep the pushing member 430 and the first through hole 221 aligned during the loading process and the surgical process, so that the adjusting member 420 can smoothly extend out of the first occluding head 220 from the first through hole 221. Moreover, even during the operation, when there is an improper force, since the step of the distal end of the pushing member 430 abuts against the step of the first through hole 221, the pushing member 430 is prevented from extending from the first through hole 221 to damage the first occluding head 220.

Figure 19:
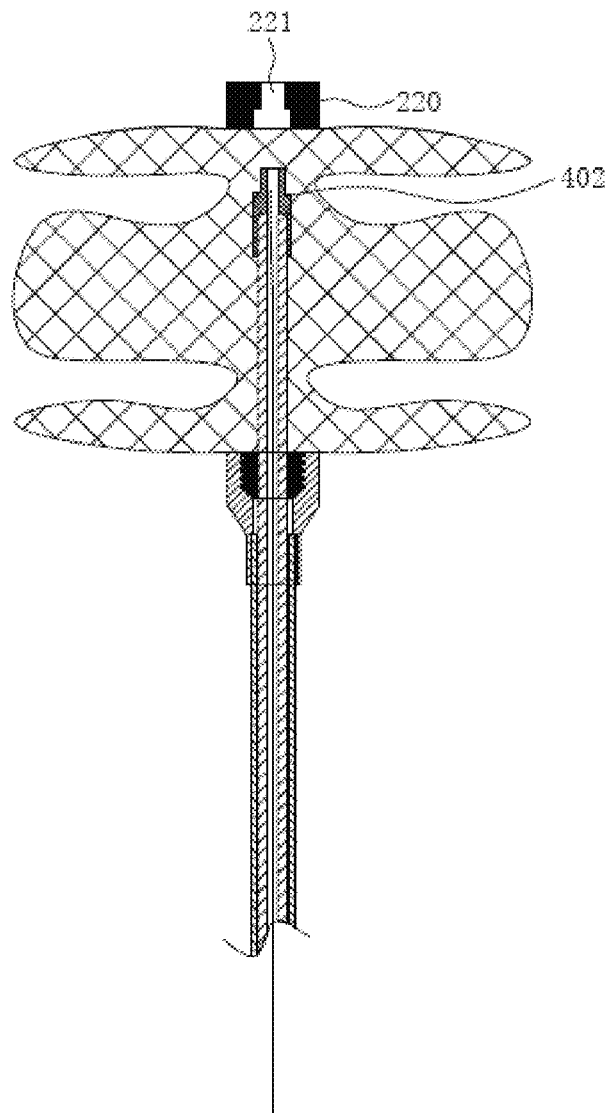
FIG. 19 is a schematic structural diagram of a first occluding head of an occluder and a pushing member according to another implementation.
Figure 20:
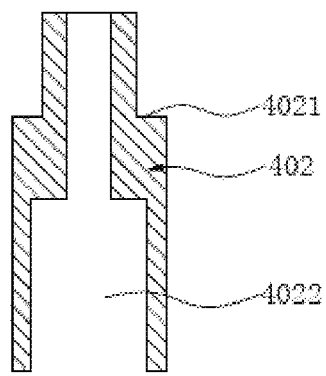
FIG. 20 is a schematic structural diagram of a transition member according to an implementation.

In an implementation, referring to FIG. 19, the first through hole 221 is a stepped hole having a larger sized end at the proximal end and a smaller sized end at the distal end. A hole wall of the stepped hole has a step. The pushing member 430 is a hollow cylindrical tube member. The conveying device 40 further includes a transition member 402. Referring to FIG. 20, the transition member 402 has a hollow cylindrical structure with a "convex" shape in cross section, a step 4021 is formed at a distal end of an outer wall of the transition member 402, and the step 4021 surrounds a peripheral surface of the distal end of the transition member 402. The middle portion of the transition member 402 is provided with an opening 4022 extending axially from the distal end to the proximal end of the transition member 402. The opening 4022 is generally "convex" shaped in cross section, and the aperture 4012 has a small end at the distal end and a large end at the proximal end. The shape and size of the large end of the opening 4022 matches the shape and size of the distal end of the pushing member 430, so that the transition member 402 can be sleeved on the distal end of the pushing member 430 and fixedly connected to the pushing member 430. During the loading, pushing and releasing processes, the distal end of the transition member 402 extends into the first through hole 221, and the step 4021 of the transition member 402 abuts against the step of the first through hole 221. In this way, not only the operation is facilitated, but damage to the first occluding head 220 and/or the adjusting member 420 is avoided. Meanwhile, the pushing member 430 has a very small outer diameter, which is usually less than 1 mm, it is very difficult to form a step on the outer wall of the pushing member 430, the process requirements are high, and it is difficult to ensure the accuracy requirements. The transition member 402 is additionally arranged to avoid processing the distal end of the pushing member 430 to form a step. Thus, the additional arrangement of the transition member 402 can reduce the processing difficulty, facilitate the improvement of the preparation efficiency, ensure the accuracy, and improve the production yield.

It will be appreciated that when the first through hole 221 is a trapezoidal hole, the aperture D1 of the first through hole 221 refers to a minimum width in the radial direction of the first through hole 221. When the first through hole 221 is a stepped hole, the aperture D1 of the first through hole 221 refers to the aperture of a smaller portion of the first through hole 221, i.e. the radial width of a portion of the first through hole 221 away from the second occluding head 230 is D1.

Referring again to FIGS. 4 and 5, the conveying device 40 further includes a limiting assembly 403. The limiting assembly 403 is configured to limit the adjusting member 420 and the pushing member 430 to avoid incorrect operation resulting in poor release of the occluder 20.

The limiting assembly 403 includes a clamping member 4031 and a lock-up member 4032 connected to the clamping member 4031. The lock-up member 4032 is configured to adjust a clamping force of the clamping member 4031 to achieve limiting or non-limiting. The clamping member 4031 is arranged in the housing 411. In an implementation, the clamping member 4031 includes a first clamping portion and a second clamping portion, a receiving region is formed between the first clamping portion and the second clamping portion, the pushing member 430 extends into the receiving region. The lock-up member 4032 is a locking wheel, the lock-up member 4032 is sleeved on the first clamping portion and the second clamping portion simultaneously, and the proximity of the first clamping portion and the second clamping portion is adjusted by rotating the lock-up member 4032, so that the size of the receiving region can be controlled. When a radial dimension of the receiving region is greater than that of the pushing member 430, the pushing member 430 may be displaced in response to the displacement of the pushing control member 460. When the size of the receiving region is smaller than the radial dimension of the pushing member 430, the pushing member 430 cannot be displaced, i.e. is limited. On this basis, when the lock-up member 4032 is continuously rotated to further lock the first clamping portion and the second clamping portion, the adjusting member 420 is clamped so as not to be displaced, i.e. is limited.

The housing 411 of the operating handle 410 is provided with a first operating window, the upper cover 412 is provided with a second operating window, and the first operating window and the second operating window are opposite to each other.

The lock-up member 4032 is arranged in the housing 411, and the lock-up member 4032 extends from the first operating window and the second operating window to facilitate operation.

The conveying device 40 of the above-described occluding system 100 is capable of conveying the occluder 20 to the lesion site and controlling the displacement of the adjusting member 420 after the occluder 20 is pushed out of the conveying sheath 490 so as to return the occluder 20 to the expanded state, thereby achieving the shaping of the occluder 20. The operation is convenient and reliable. Moreover, the occluder 20 has a simple structure without an additional forming auxiliary structure.

In an implementation, the occluder 20 is a cardiac occluder, such as an atrial septal defect occluder, a ventricular septal defect occluder, and a left atrial appendage occluder.

In an implementation, the occluder 20 is a vascular occluder that may be configured to block blood flow to treat vascular malformations or to block blood flow to treat tumors, etc.

Figure 21:
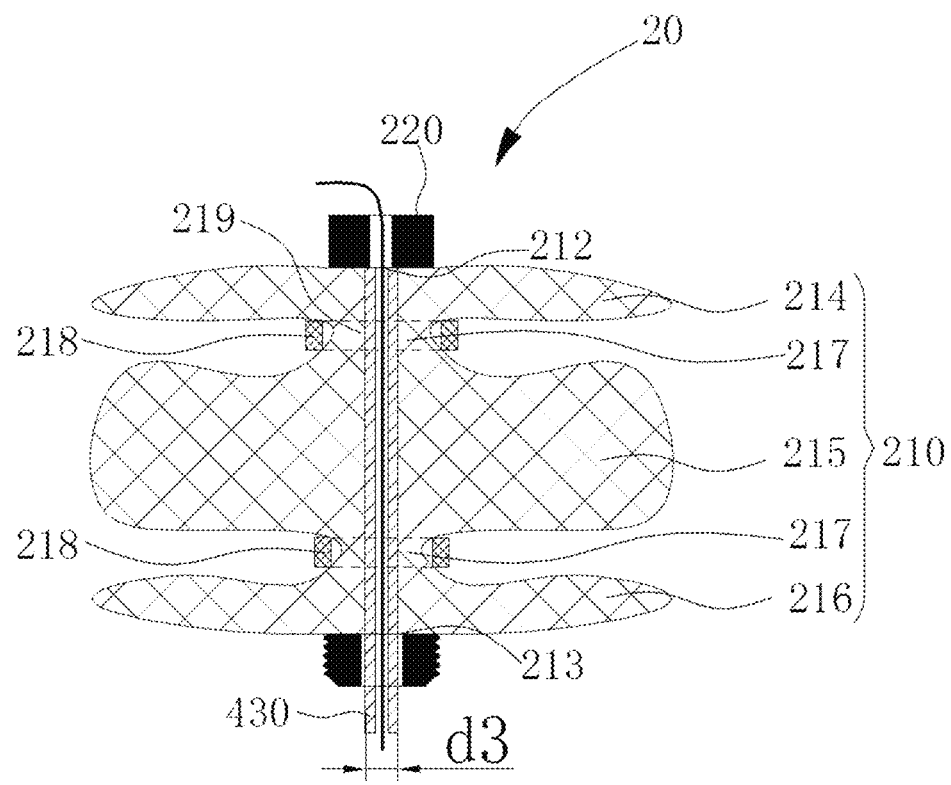
FIG. 21 is a schematic structural diagram of an occluder according to another implementation.

Referring to FIG. 21, in an implementation, the occluder 20 further includes a fixing member 218. The fixing member 218 is sleeved on the waist portion 217 of the occluding frame 210. The middle portion of the fixing member 218 is formed with a channel 219 that extends axially from the distal end of the fixing member 218 to the fixing member 218. The inner cavity 211 (not shown in FIG. 21) of the occluding frame 210, the first opening 212, the second opening 213, and the channel 219 are communicated to form a path.

The number of fixing members 218 corresponds to the number of waist portions 217. In the implementation shown in FIG. 21, there are two waist portions 217, and there are two fixing members 218 correspondingly.

In another implementation, there are a plurality of middle portion occluding units 215, there are more than two waist portions 217, and the plurality of middle portion occluding units 215 and the plurality of waist portions 217 are alternately arranged in the axial direction. The distal-most middle portion occluding unit 215 is connected to the first occluding unit 214 through the waist portion 217, and the proximal-most middle portion occluding unit 215 is connected to the second occluding unit 216 through the waist portion 217. A plurality of fixing members 218 are respectively sleeved on the plurality of waist portions 217. The channel 219 should be large enough so that when the fixing members 218 are placed on the waist portions 217, a space remains in the middle portion of the channel 219.

The axial lengths of the plurality of middle portion occluding units 215 may be equal or different. In the plurality of middle portion occluding units 215, all the axial length of the middle portion occluding units 215 may be greater than that of the first occluding unit 214 and the second occluding unit 216, or the axial length of some middle portion occluding units 215 may be greater than that of the first occluding unit 214 and the second occluding unit 216, and the axial length of some middle portion occluding units 215 is equal to that of the first occluding unit 214 and the second occluding unit 216.

The first opening 212, the second opening 213, the channel 219, the first through hole 221, and the second through hole 231 are coaxial such that when the pushing member 430 is axially displaced from the second through hole 231 into the path formed by communicating the inner cavity 211, the first opening 212, the second opening 213, and the channel 219 during loading, the distal end of the pushing member 430 abuts against the first occluding head 220 to assist in loading and subsequent shaping. By sleeving the fixing member 218 on the waist portion 217, the fixing member 218 further fixes the above-described path, i.e. further fixes a path in which the pushing member 430 moves inside the occluding frame 210, thereby avoiding damage to the occluding frame 210 caused by hitting the occluding frame 210 due to deviation of the pushing member 430 from a preset direction.

Therefore, the locking member may be omitted in the above-described occluder 20, and loading of the occluder 20 may be conveniently achieved by omitting the locking member. The occluder 20 in which the locking member is omitted is more flexible, facilitates passage through a curved vascular path, or facilitates adaptation to a curved vascular lesion.

In an implementation, the fixing member 218 is a sleeve formed of a high-molecular material, and a channel extending from a distal end to a proximal end of the sleeve is formed in a middle portion of the sleeve. The sleeve is sleeved on the waist portion 217, and an inner wall of the sleeve is in contact with the peripheral surface of the waist portion 217. The channel should be large enough so that when the sleeve is sleeved on the waist portion 217, a space remains in the channel to facilitate passage of the pushing member 430. However, the channel should not be too large, otherwise there is less limitation to the pushing member 430. A high-molecular material forming the sleeve is a bioabsorbable high-molecular material so that the entire occluder 20 is bioabsorbable.

The axial length of the sleeve is less than or equal to that of the waist portion 217. In an implementation, the ratio of the axial length of the sleeve to the axial length of the waist portion 217 is 1:(2-5), so as to avoid influence on the overall flexibility of the occluder 20 due to over-large axial length of the sleeve, and also avoid difficult processing due to over-small axial length of the sleeve.

Figure 22:
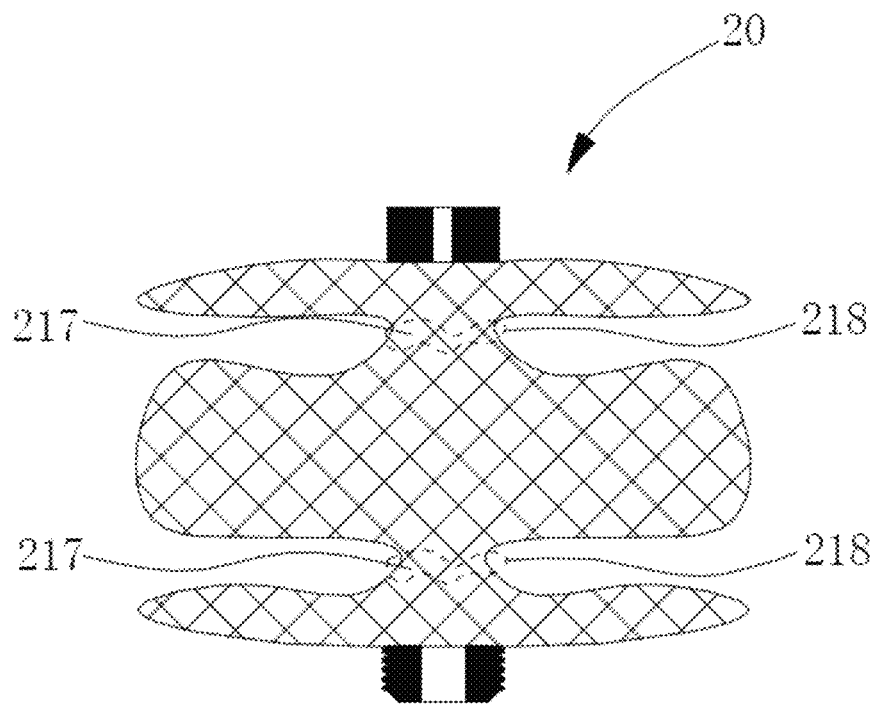
FIG. 22 is a schematic structural diagram of an occluder according to another implementation.

In an implementation, referring to FIG. 22, the fixing member 218 is an annular structure formed by winding a high-molecular wire around the periphery of the waist portion 217. The high-molecular wire is a flexible wire such as a high-molecular fiber wire and a high-molecular medical suture. In an implementation, the high-molecular wire is an absorbable high-molecular wire so that the entire occluder 20 is bioabsorbable. The high-molecular wire such as the high-molecular fiber wire and the high-molecular medical suture is relatively soft, and the annular structure formed by winding the high-molecular wire around the periphery of the waist portion 217 is also relatively soft, so that the arrangement of the fixing member 218 does not significantly increase the overall rigidity of the occluder 20, and even if the number of fixing members 218 is greater than 2, the occluder 20 can still keep sufficient flexibility. Moreover, the mode of forming the fixing member 218 sleeved on the waist portion 217 with the high-molecular wire is simple in preparation or processing and easy in operation.

Figure 23:
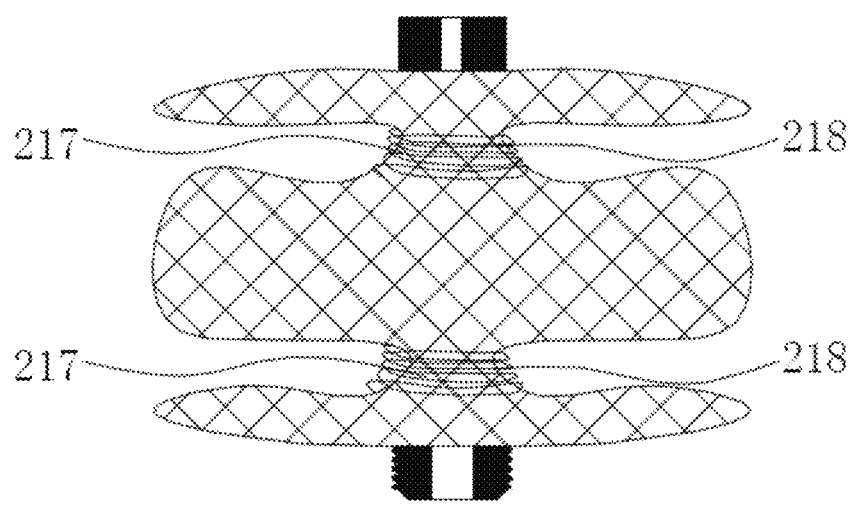
FIG. 23 is a schematic structural diagram of an occluder according to another implementation.

The high-molecular wire is wound around the waist portion 217 for one or more circles (as shown in FIG. 23) to form the fixing member 218. It will be appreciated that the winding tightness of the high-molecular wire should be suitable so that, on the one hand, the high-molecular wire can be more reliably held in place with the waist portion 217, and, on the other hand, the channel formed by the high-molecular wire after the high-molecular wire is wound around the waist portion 217 should be large enough to facilitate the passage of the pushing member 430.

When the high-molecular wire is wound around the waist portion 217 for one circle, a wire diameter of the high-molecular wire is relatively large. When the high-molecular wire is wound around the waist portion 217 for more circles, a high-molecular wire having a small wire diameter may be used. The high-molecular wire is wound around the waist portion 217 for more circles to form the fixing member 218, so as to facilitate the reliable connection between the fixing member 218 and the waist portion 217.

In an implementation, whether the fixing member 218 is the sleeve formed of the high-molecular material or the annular structure formed by winding the high-molecular wire around the periphery of the waist portion 217, the width of the channel of the fixing member 218 is D6, and in a natural state, the radial width of the waist portion is D7. The outer diameter D3 of the pushing member 430 is less than D6, so that the pushing member 430 smoothly passes through the fixing member 218. D7 is greater than D6 to facilitate the reliable connection between the fixing member 218 and the waist portion 217.

In an implementation, D3 is 0.1 mm-4 mm less than D6, D7 is 2 mm-60 mm greater than D6, so that the pushing member 430 can pass smoothly through the fixing member 218 and the fixing member 218 can be reliably connected to the waist portion 217, thereby preventing the fixing member 218 from falling off the waist portion 217 when the occluder 20 is axially stretched and loaded into the conveying sheath 490, which is particularly important for an implementation where the fixing member 218 is the annular structure formed by winding the high-molecular wire around the periphery of the waist portion 217.

The high-molecular material does not have elasticity and shape memory features. Although the occluding frame 210 made of the high-molecular material is shaped, it is limited by the characteristics of the high-molecular material, the stability of the occluding frame 210 is worse than that of the shape memory metal material or alloy material. Especially when the locking member is omitted, the stability of the occluding frame 210 made of the high-molecular material will be lower. Further, it is particularly important to improve the stability of the occluding frame 210 when the number of middle portion occluding units 215 and waist portions 217 is large, resulting in a larger axial length of the occluder 20. The waist portion 217 is sleeved with the fixing member 218, which is equivalent to axially dividing the occluding frame 210 into a plurality of portions with a relatively small axial length, thereby facilitating the improvement of the overall stability of the occluding frame 210, so that the occluder 20 can stably keep a preset shape in the lesion site, thereby improving the occluding effect.

In the above-described occluder 20, the fixing member 218 is sleeved on the waist portion 217, and the fixing member 218 facilitates fixing the displacement path of the pushing member 430 at the occluding frame 210, so that the pushing member 430 is displaced along the fixed path until the distal end of the pushing member 430 abuts against the first occluding head 220 of the occluder 20, so as to achieve the axial stretching of the occluder 20 to facilitate loading. Moreover, due to the limitation of the fixing member 218 during the loading process, it is possible to prevent the distal end of the pushing member 430 from coming out of abutment with the first occluding head 220 due to slipping or improper operation, so that the pushing member 430 can be kept in abutment with the first occluding head 220 without deviation, thereby ensuring that the loading of the occluder 20 can be performed smoothly.

Moreover, after the conveying of the occluder 20 to the lesion site through the conveying sheath 490 and before confirming whether the occluder 20 is in an accurate position after being pushed out of the conveying sheath 490, the pushing member 430 can be kept in abutment with the first occluding head 220 without deviation due to the limitation of the fixing member 218, so that the occluder 20 can be reliably kept in the axially stretched state to facilitate an operator to adjust the position of the occluder 20.

Meanwhile, the fixing member 218 facilitates fixing of relative positions of the pushing member 430 and the first occluding head 220, and facilitates avoiding unnecessary hit of the pushing member 430 against the first occluding head 220 and/or the occluding frame 210, so as to avoid damaging the first occluding head 220 and/or the occluding frame 210.

Therefore, the locking member can be omitted in the occluder 20. The occluder 20 of the occluding system 100 cooperates with the conveying device 40 to facilitate convenient and reliable loading and forming of the occluder 20.

In an implementation, when there is one middle portion occluding unit 215, there are two waist portions 217, and the fixing member 218 is an annular structure formed by winding the high-molecular wire around the periphery of the waist portions 217, the tightness of the high molecular wires wound as the two fixing members 218 is not equal, the width D6 of the channels of the two fixing members 218 is not equal, the tightness of the fixing member 218 at the distal end is smaller, and the value of D6 is larger. This arrangement makes it convenient to adjust the axial length of the occluder 20 while ensuring convenient loading and forming, so that the surgery can be performed smoothly.

All features of the above-mentioned embodiments may be combined in any combination. In order to simplify the description, all possible combinations of all the features in the above-mentioned embodiments are not described. However, insofar as the combinations of these features do not contradict, they should be considered to be the scope contained in this description.

The above-described embodiments are only a few implementations, which are described in greater detail but are not to be construed as limiting. It will be appreciated by those of ordinary skill in the art that numerous variations and modifications may be made to the embodiments without departing from the scope of the embodiments.

The invention claimed is:

1. A conveying device for conveying an implantable instrument, comprising:
    an adjusting member, having a distal end and a proximal end, the distal end of the adjusting member having a pre-bending portion in a natural state;
    an operating handle, the proximal end of the adjusting member being connected to the operating handle;
    a pushing member,
    wherein the pushing member is a hollow tube member comprising a distal end, a proximal end, and a lumen extending from the distal end to the proximal end of the pushing member, and the adjusting member is slidably accommodated within the lumen of the pushing member;
    a pushing control member,
    wherein the pushing control member is arranged on the operating handle, the proximal end of the pushing member is connected to the pushing control member, the pushing control member is configured to control the displacement of the pushing member; and
    an adjusting control member, arranged on the operating handle and connected to the proximal end of the adjusting member for controlling the displacement of the adjusting member such that an inner side surface of the pre-bending portion of the adjusting member abuts against a distal end surface of the implantable instrument to achieve shaping of the implantable instrument;
    wherein the conveying device further comprises an interlocking mechanism that is arranged on the operating handle, and
    wherein the interlocking mechanism comprises at least two magnetic components that are arranged on the adjusting control member and the pushing control member, respectively, configured to enable the detachable locking of the adjusting member and the pushing member.

2. The conveying device according to claim 1, wherein the pre-bending portion is an arc-shaped rod or an arc-shaped wire at an angle of 40-90°.

3. The conveying device according to claim 1, wherein the number of magnetic components on the adjusting control member and the number of magnetic components of the pushing control member are equal or unequal, the magnetic components on the adjusting control member and the magnetic components of the pushing control member are arranged oppositely, and opposite parts of the magnetic components on the adjusting control member and the magnetic components of the pushing control member have different polarities.

4. The conveying device according to claim 3, wherein the operating handle comprises a housing and an upper cover detachably connected to the housing, wherein the housing and the upper cover form a first track, a second track parallel to the first track is arranged in the housing, the adjusting control member and the pushing control member are slidably arranged on the second track, the adjusting control member comprises a first operating portion that is located outside the operating handle, the pushing control member comprises a second operating portion that is located outside the operating handle, and the adjusting control member and the pushing control member are axially displaceable along the first track and the second track by operating the first operating portion and the second operating portion.

5. The conveying device according to claim 4, wherein the interlocking mechanism comprises a locking member that is located outside the operating handle and detachably connected to the first operating portion and the second operating portion for locking the adjusting control member and the pushing control member.

6. The conveying device according to claim 1, wherein the conveying device further comprising a limiting assembly, the limiting assembly comprises a clamping member and a lock-up member connected to the clamping member, the pushing member passes through the clamping member, and the lock-up member is configured to adjust a clamping force of the clamping member to achieve limiting or non-limiting displacements of the adjusting member and the pushing member.

7. The conveying device according to claim 1, wherein further comprising a transition member that is sleeved on the distal end of the pushing member and provided with an opening communicated with the lumen of the pushing member.

8. The conveying device according to claim 7, wherein the transition member has a hollow cylindrical structure with a convex shape in cross section, a step is formed at a distal end of an outer wall of the transition member, and the step surrounds a peripheral surface of the distal end of the transition member.

9. The conveying device according to claim 8, wherein the middle portion of the transition member is provided with an opening extending axially from the distal end to an proximal end of the transition member, the opening is convex shaped in cross section, and the opening has a small end at the distal end of the transition member and a large end at the proximal end of the transition member.

10. The conveying device according to claim 1, wherein the implantable instrument is a cardiac occluder or vascular occluder.

11. The conveying device according to claim 1, wherein the adjusting member is an elongated rod member and the distal end of the adjusting member is free.

12. The conveying device according to claim 1, wherein the adjusting member is an elongated, rigid metal rod or wire, and a material of the adjusting member is a shape memory metal material or a shape memory alloy material.

13. The conveying device according to claim 1, wherein the pushing member has an outer diameter D3 and an inner diameter D4, an outer diameter of the adjusting member is D5, D3>D4>D5.

14. The conveying device according to claim 1, wherein the implantable instrument is an occluder, the occluder comprises an occluding frame, a first occluding head and a second occluding head, the first occluding head and the second occluding head are respectively arranged at two opposite ends of the occluding frame, the first occluding head is provided with a first through hole, the second occluding head is provided with a second through hole, the first through hole has an aperture D1, and the second through hole has an aperture D2, the pushing member has an outer diameter D3 and an inner diameter D4, an outer diameter of the adjusting member is D5, D2>D3>D1>D4>D5.

15. The conveying device according to claim 1, wherein the conveying device further comprises a conveying member, the conveying member has a distal end and a proximal end, and the proximal end of the conveying member is connected to the operating handle, the distal end of the conveying member is provided with a connecting portion, and an inner wall of the connecting portion is provided with internal threads.

16. The conveying device according to claim 15, wherein the conveying member is a hollow tube member.

17. The conveying device according to claim 15, wherein the conveying member is a hollow stainless steel spring tube, or the conveying member is a hollow nickel-titanium cable.

18. A conveying device for conveying an implantable instrument, wherein comprising:
  an adjusting member, having a distal end and a proximal end;
  an operating handle, the proximal end of the adjusting member being connected to the operating handle;
  a pushing member and a pushing control member, wherein the pushing control member is arranged on the operating handle, a proximal end of the pushing member is connected to the pushing control member, the pushing control member has an inner cavity, and the adjusting member passes through the pushing member;
  an adjusting control member, arranged on the operating handle and connected to the proximal end of the adjusting member for controlling the displacement of the adjusting member; and an interlocking mechanism that is arranged on the operating handle for keeping the adjusting member and the pushing member detachably locked;
  wherein the interlocking mechanism comprises at least two magnetic components that are arranged on the adjusting control member and the pushing control member, respectively, the number of magnetic components on the adjusting control member and the number of magnetic components of the pushing control member are equal or unequal, the magnetic components on the adjusting control member and the magnetic components of the pushing control member are arranged oppositely, and opposite parts of the magnetic components on the adjusting control member and the magnetic components of the pushing control member have different polarities.

19. The conveying device according to claim 18, wherein the operating handle comprises a housing and an upper cover detachably connected to the housing, wherein the housing and the upper cover form a first track, a second track parallel to the first track is arranged in the housing, the adjusting control member and the pushing control member are slidably arranged on the second track, the adjusting control member comprises a first operating portion that is located outside the operating handle, the pushing control member comprises a second operating portion that is located outside the operating handle, and the adjusting control member and the pushing control member are axially displaceable along the first track and the second track by operating the first operating portion and the second operating portion.

* * * * *